US008420328B2

(12) United States Patent
Chen et al.

(10) Patent No.: US 8,420,328 B2
(45) Date of Patent: Apr. 16, 2013

(54) REUSABLE NANOWIRE FIELD EFFECT TRANSISTOR SYSTEM FOR DETECTING BIOMOLECULAR INTERACTIONS

(75) Inventors: Yit-Tsong Chen, Taipei County (TW); Chien-Yuan Pan, Taipei (TW); Tsung-Wu Lin, Taipei (TW)

(73) Assignee: Academia Sinica, Taipei (TW)

( * ) Notice: Subject to any disclaimer, the term of this patent is extended or adjusted under 35 U.S.C. 154(b) by 279 days.

(21) Appl. No.: 12/778,619

(22) Filed: May 12, 2010

(65) Prior Publication Data

US 2011/0281288 A1    Nov. 17, 2011

(51) Int. Cl.
G01N 33/53    (2006.01)
(52) U.S. Cl.
USPC ........ 435/7.1; 435/6.19; 435/287.1; 427/2.13
(58) Field of Classification Search ........................ None
See application file for complete search history.

(56) References Cited

U.S. PATENT DOCUMENTS

2004/0136866 A1*   7/2004  Pontis et al. .................... 422/57
2010/0194409 A1*   8/2010  Gao et al. ...................... 324/693

OTHER PUBLICATIONS

Lin et al., A reversible surface functionalized nanowire transistor to study protein-protein interactions, available online May 12, 2009, Nano Today, 4: pp. 235-243.*
Jung et al., High throughput analysis of GST-fusion protein expression and activity-dependent protein interactions on GST-fusion protein arrays with a spectral surface plasmon resonance biosensor, 2006, Proteomics, 6: pp. 1110-1120.*
Zheng et al., "Multiplexed Electrical Detection of Cancer Markers with Nanowire Sensor Arrays," Nature Biotechnology, 23(10): 1294-1301 (2005).
Lin et al., "A Reversible Surface Functionalized Nanowire Transistor to Study Protein-Protein Interactions," Nano Today, 4:235-243 (2009).
Lichty et al., "Comparison of Affinity Tags for Protein Purification," Protein Expression and Purification, 41:98-105 (2005).
Lin et al., "Label-Free Detection of Protein-Protein Interactions Using Calmodulin-Modified Nanowire Transistor," PNAS, 107(3):1047-1052 (2010).

* cited by examiner

Primary Examiner — N. C. Yang
(74) Attorney, Agent, or Firm — Occhiuti Rohlicek & Tsao LLP

(57) ABSTRACT

A reusable nanowire field effect transistor for detecting biomolecular interactions. The field effect transistor contains nanowire covalently linked to a docking molecule, which is capable of binding to an anchor molecule in a reversible manner, i.e., at an association constant of $10^5$ to $10^9$ $M^{-1}$.

20 Claims, 6 Drawing Sheets

REUSABLE NANOWIRE FIELD EFFECT TRANSISTOR SYSTEM FOR DETECTING BIOMOLECULAR INTERACTIONS

BACKGROUND OF THE INVENTION

In the post-genomic era, efforts have been focused on unraveling the complex interactions of biomolecules (e.g., proteins, nucleic acids, polysaccharides, and lipids) that occur in living cells. Understanding these biomolecular interactions will assist in deciphering disease mechanisms and developing new diagnostic/therapeutic methods.

It is of great importance to develop new approaches and devices suitable for detecting biomolecular interactions in a rapid and accurate manner.

SUMMARY OF THE INVENTION

One aspect of this invention relates to a reusable nanowire field effect transistor (NW-FET) system for detecting a biomolecular interaction. This system contains a field effect transistor including a nanowire, a docking molecule covalently linked to the nanowire, and optionally, a conjugate (e.g., a fusion protein) composed of an anchor molecule and a bait molecule. The docking molecule is capable of binding to the anchor molecule in a reversible manner, i.e., at an association constant of $10^5$ to $10^9$ $M^{-1}$ (e.g., $10^6$ to $10^8$ $M^{-1}$). Examples of docking/anchor molecules for use in this invention include, but are not limited to, glutathione/glutathione S-transferase, maltose/maltose binding protein, imidazole/polyhistidine, chitin/chitin binding protein, calcium/calmodulin, and covalent yet dissociable peptide/InaD protein. In one example, the docking molecule is glutathione (GSH) and the anchor molecule is glutathione S-transferase (GST), which can form a fusion protein with a bait protein molecule. The nanowire may be made from silicon, carbon, tin dioxide, or indium oxide.

Another aspect of the present invention features a method for detecting the presence of a target molecule in a sample. The method includes (i) providing any of the NW-FET systems described above, in which the docking molecule is bound to a conjugate containing the anchor molecule and a bait molecule capable of binding to the target molecule, (ii) contacting the system with a sample suspected of containing the target molecule, and (iii) detecting a conductivity change (e.g., a current change or a conductance change) of the field effect transistor in the NW-FET system after the contacting step. When a conductivity change is observed, it indicates that the sample contains the target molecule, which can be a protein molecule, a nucleic acid molecule, a polysaccharide molecule, or a lipid molecule. In one example, this method further includes, after the detecting step, correlating a level of the conductivity change with a concentration of the target molecule in the sample so as to quantify the target molecule. After the detecting step, the NW-FET system can be washed with a solution containing the docking molecule to release the conjugate bound to the field effect transistor.

Also within the scope of this invention is a method for identifying a compound capable of binding to a molecule of interest. The method includes (i) providing any of the NW-FET systems described above, in which the docking molecule is bound to a conjugate containing the anchor molecule and a molecule of interest, (ii) contacting the system with a sample containing a plurality of compounds, (iii) determining binding of a compound to the molecule of interest based on a conductivity change of the system, and (iv) collecting the compound for characterization.

The details of several embodiments of the invention are set forth in the description below. Other features or advantages of the present invention will be apparent from the following drawings and actual examples, and also from the appended claims.

BRIEF DESCRIPTION OF THE DRAWINGS

The drawings are first described.

DETAILED DESCRIPTION OF THE INVENTION

Figure 1:
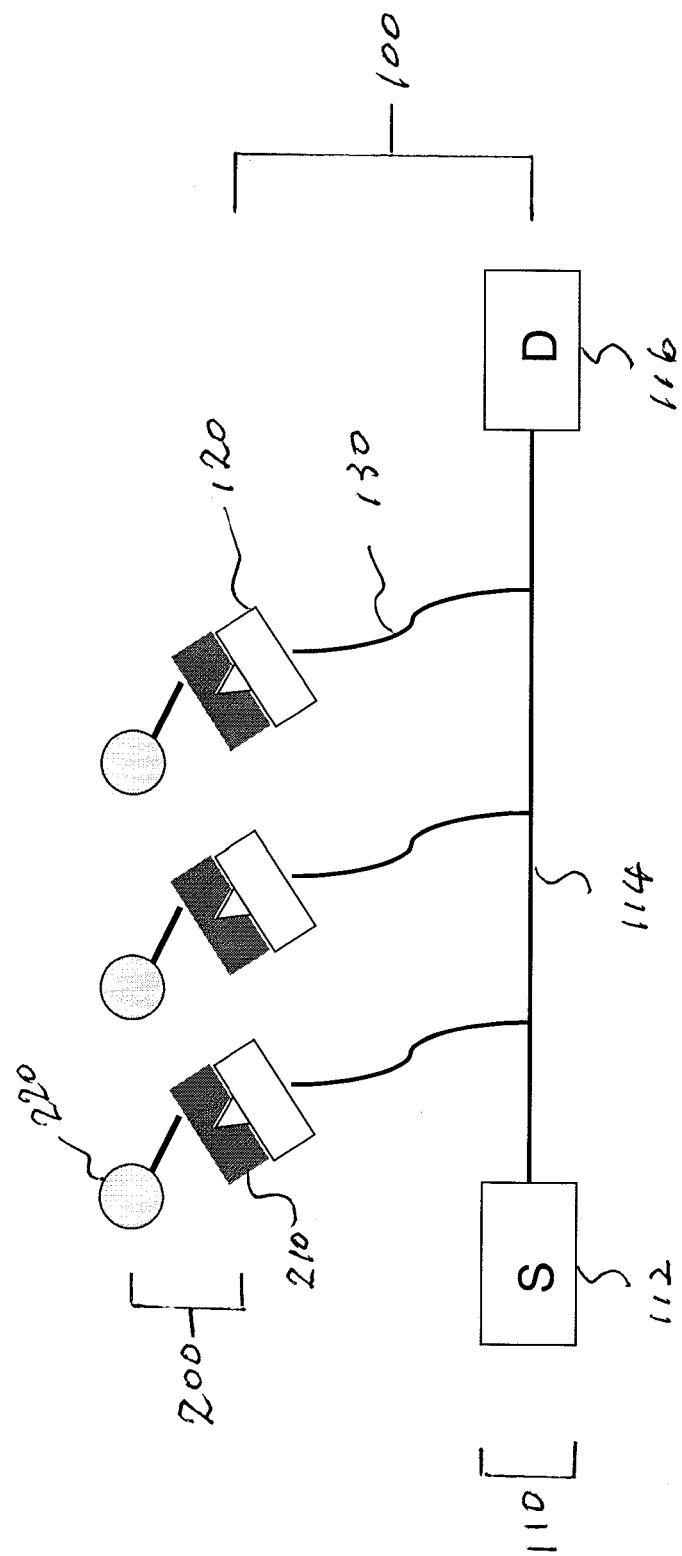
FIG. 1 is a diagram of a nanowire field effect transistor (NW-FET) system, in which the nanowire is covalently linked to GSH as a docking molecule. The GSH is associated with anchor molecule GST, which is conjugated with a bait molecule. S: source electrode; D: drain electrode.

Disclosed herein is a reusable NW-FET system useful in detecting biomolecular interactions. As shown in FIG. 1, this system (100) includes NW-FET 110 covalently bound to docking molecule 120 preferably via linker 130.

NW-FET 110 includes nanowire 114 that connects source electrode 112 and drain electrode 116. Nanowire 114 can be made from any material suitable for preparing semiconductors, including, but are not limited to, silicon (e.g., doped with boron or phosphorus), tin dioxide, indium oxide, and carbon. A nanowire made from any of the suitable materials (e.g., silicon or carbon) may also contain one or more others. In one example, the nanowire in 114 is a silicon nanowire, the surface of which can be oxidized to form a silicon dioxide layer. In another example, it can be a semiconductive carbon nanotube.

Docking molecule 120 is capable of interacting with anchor molecule 210 in a reversible manner, i.e., having an association constant ($K_a$) between $10^5$ to $10^9$ $M^{-1}$. Preferably, the docking molecule used in the NW-FET system of this invention interacts with the anchor molecule at an association constant greater than $10^7$ $M^{-1}$.

As well known in the art, $K_a$ refers to the binding affinity of two molecules A and B at equilibrium of association to form C, i.e., A+B ⇌ C. It is calculated as:

$$K_a = \frac{[C]}{[A][B]}$$

In this equation, [A], [B], and [C] refer to the concentrations of free A, free B, and complex C, respectively, when the association between A and B reaches equilibrium. $K_a$ can be determined via any conventional method. See, e.g., Telmer et al., *J. Biol. Chem.* 278(36): 34555-34567 (2003) and Sun et al., *Biochem. J.* 326:193-196 (1997).

Docking molecule 120 can be a protein molecule, a nucleic acid molecule, a polysaccharide molecule, or a small molecule (MW<2,000) that reversibly interacts with a cognate anchor molecule, which can be a protein, a nucleic acid, a sugar, or a small molecule. Such docking/anchor pairs are well known in the art. See, e.g., Lichty et al., *Protein Expression and Purification* 41:98-105, 2005. The term "protein," "nucleic acid", and "polysaccharide" used herein refer to polymers (including oligomers) of amino acids, nucleotides, and monosaccharides, respectively. An oligomer typically includes up to 50 monomer units (e.g., 30, 20, 10, or less). Suitable docking molecules include, but are not limited to, a member of the molecule pair GSH/GST, maltose/maltose binding protein, imidazole/polyhistidine, chitin/chitin binding protein, calcium/calmodulin, or covalent yet dissociable (CYD) peptide/InaD protein. Preferably, neither docking molecule 120 nor anchor molecule 210 is an antibody.

Docking molecule 120 is immobilized onto the nanowire of the NW-FET system via covalent bonding, preferably through a chemical linker (130 in FIG. 1). Conventional methods can be used to prepare the docking molecule-immobilized NW-FET, depending on the nature of the docking molecule and the material used for making the NW-FET. In general, a layer of a first linking compound that includes a functional group can be coated onto the nanowire, when necessary. This functional group can then form a covalent bond with a docking molecule so as to immobilize it onto the nanowire. Optionally, the first linking compound can link to a second linking compound, which, in turn, attaches to the docking molecule via a covalent bond. The second linking compound either provides a functional group for reacting with the docking molecule or serves as a spacer to facilitate binding between the docking molecule and the anchor molecule. When docking molecule 120 is a protein molecule, it can be attached to a NW-FET by the method described in Lin et al. (2009) *Nano Today* 4, 235-243. When necessary, a docking molecule can be modified prior to its attachment to the nanowire so as to minimize property changes due to immobilization.

The above-described NW-FET system 100, with docking molecule 120 immobilized, can be used in a method for detecting a target molecule, which preferably is a biomolecule (e.g., protein, nucleic acid, polysaccharide, or lipid). An example of this detecting process is illustrated in FIG. 2.

Figure 2:
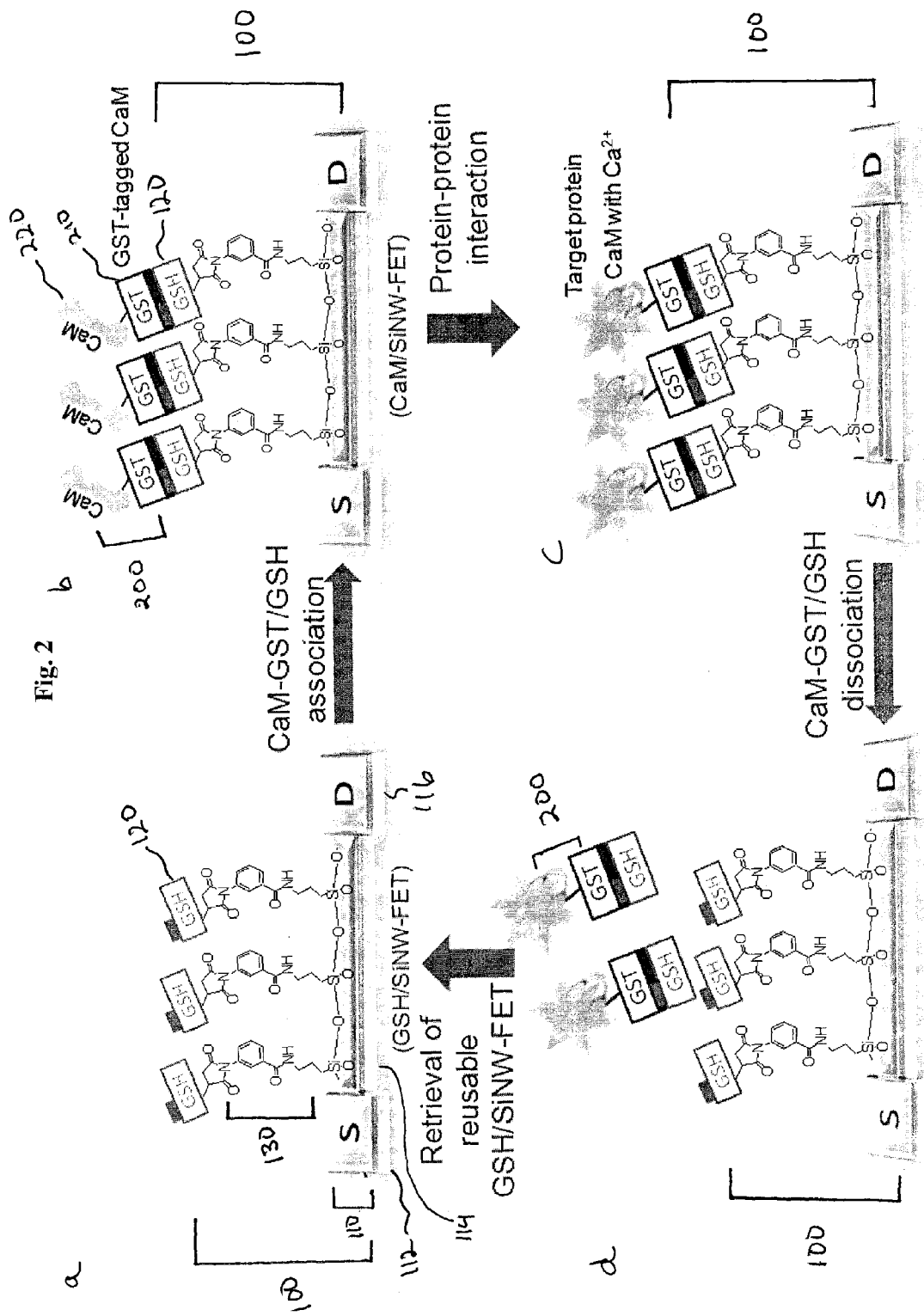
FIG. 2 is a diagram of a reusable GSH immobilized NW-FET for detecting biomolecular interactions. Panel a: a GSH immobilized NW-FET system. Panel b: association of the GSH immobilized NW-FET with a fusion protein containing GST and calmudolin (CaM, a bait molecule) via GSH/GST interaction. Panel c: binding of a target protein to the GST-CaM fusion protein-associated NW-FET via interaction between the target protein and CaM. Panel d: release of the GST-CaM fusion protein, associated with the target protein, from the NW-FET system.

Referring to FIG. 2, panel a to panel b, NW-FET system 100 is first exposed to conjugate 200, which contains anchor molecule 210 and bait molecule 220. As used herein, "conjugate" refers to two entities that are associated, preferably via a covalent bond, either directly or through a linker. A conjugate can be prepared by linking two entities (e.g., protein, nucleic acid, or polysaccharide) via a chemical reaction. If the conjugate is a fusion protein, it can be prepared by conventional recombinant technology. Bait molecule 220 in conjugate 200 is a molecule capable of binding to the target molecule. Thus, the type of the bait molecule to be used for constructing conjugate 200 shall depend on the type of the target molecule to be detected.

After association with conjugate 200, NW-FET system 100 is then brought into contact with a sample suspected of containing the target molecule. See FIG. 2, panel b to panel c. Binding of the target molecule to the bait molecule in conjugate 200 would affect the size, shape, and surface potential of the conductive channel formed by the nanowire in NW-FET system 100, resulting in a change of its conductivity. See Lin et al., *Proc. Natl. Acad. Sci. USA* 107, 1047-1052, 2010. Thus, a conductivity change in NW-FET system 100, which can be monitored by measuring its current or conductance between source electrode 112 and drain electrode 116, indicates the presence of the target molecule in the sample.

As mentioned above, docking molecule 120 interacts with anchor molecule 210 in a reversible manner. Thus, conjugate 200 (bound to the target molecule) can be released from NW-FET system 100 via dissociation between docking molecule 120 in NW-FET system 100 and anchor molecule 210 in conjugate 200. This can be achieved by washing conjugate 200-associated NW-FET system 100 with a solution containing the docking molecule at a suitable concentration so as to produce free NW-FET system 100 (no longer bound to conjugate 200). See FIG. 2, panel c to panel d. This free NW-FET system 100 can be re-used in a subsequent assay for detecting presence of a target molecule. Clearly, the reversible interaction between docking molecule 120 and anchor molecule 210 contributes to an advantage of the NW-FET system of this invention, i.e., reusability. Indeed, one embodiment of the NW-FET system described herein (see Example 1 below) can be reused, unexpectedly, for at least 30 times.

The NW-FET system of this invention can also be used to quantify a target molecule as follows. NW-FET system 100, associated with conjugate 200, is brought into contact with a solution containing a target molecule capable of binding to conjugate 200 at a predetermined concentration. The level of the conductivity change of NW-FET system 100 after exposure to the solution is determined. A standard curve is then prepared based on the concentrations of the target molecule (e.g., log values) versus the levels of conductivity changes caused thereby. NW-FET system 100 is then exposed to a sample containing the target molecule. The level of the conductivity change is measured and the concentration of the target molecule is determined by comparing the conductivity change level with the standard curve. Since the NW-FET system of this invention is reusable, a single NW-FET system can be used in the just-described quantification assay.

In addition, the NW-FET system of this invention can be used in a screening method to identify a compound capable of binding to a molecule of interest. In this case, a molecule of interest (same as bait molecule 220) is conjugated with anchor molecule 210 to form a conjugate. After being associated with this conjugate, NW-FET system 100 is exposed to a sample containing a plurality of compounds. A conductivity change of NW-FET system 100 is monitored, which indicates binding of a compound to it. The compound bound to NW-FET system 100 is then released by a conventional method (e.g., washing with a solution containing a detergent or changing ion strength) and collected for characterization by, e.g., mass spectrometry.

Alternatively, a plurality of NW-FET system 100 can be assembled to form a biosensor chip and the above-described screening method can be performed following routine procedures, in which microchips are used. See Zheng, et al., *Nature Biotechnology* 23(10):1294-1301, 2005.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

EXAMPLE 1

Construction and Characterization of a Reusable GSH/GST Silicon Nanowire-Field Effect Transistor (SiNW-FET)

I. Prepararing a Reusable GSH/GST-SiNW-FET.

A SiNW-FET was fabricated by one of the two methods described below. First, a boron- or phosphorus-doped SiNW was synthesized catalytically (assisted by 20 nm gold nanoparticles) in a chemical vapor deposition reaction at 460° C. via a vapor-liquid-solid growth mechanism from silane ($SiH_4$) and diborane ($B_2H_6$) or phosphine ($PH_3$) precursors. Before the fabrication of the SiNW-FET devices, the as-synthesized SiNW was ultrasonicated in ethanol and then dispersed on a highly boron-doped Si wafer (1.7×1.7 $cm^2$) with a 400 nm $SiO_2$ layer. A SiNW-FET devices was fabricated following standard photolithographic procedures. See Patolsky et al. *Nat. Protoc.* 1, 1711-1724, 2006. The metal leads were made by the deposition of Ni (70 nm thick) and Al (100 nm thick). The surface of the Al layer was later oxidized to form an $Al_2O_3$ film several nanometers thick, serving as an insulating coat for the prevention of electric leakage during sensing experiments. The as-fabricated SiNW-FET chip was then annealed in a rapid thermal annealer with 10% $H_2$ and 90% $N_2$ forming gases at 360° C. for 1 min, in order to form an Ohmic contact between the Ni leads and the SiNW.

Second, a SiNW-FET was fabricated using four-inch silicon-on-insulator (SOI) wafers with a 50 nm thick Si top layer and a 400 nm thick buried oxide layer (typically having a 100 Ω·cm resistivity), following the conventional lithographic procedure. Briefly, the nanowires were defined by standard electron beam lithography and a dry-etching process in an inductively-coupled-plasma etcher with $C_4F_8$ and $SF_6$ gas mixture. The as-fabricated nanowires were thermally oxidized at 900° C. for 20 min in an $O_2$ ambient to form a 10 nm thick $SiO_2$ insulating layer to inhibit any charge transfer between the wires and surrounding molecules in the sensing experiments. The nanowires were then connected to the outside millimeter-size contact pads via heavily boron-doped micrometer-wide Si leads patterned by photolithography. The ion implantation was carried out with a nominal doping concentration of $10^{19}$ $cm^{-3}$ at an implantation energy of 11 keV which gave a doping depth of ~40 nm. The implanted ions were activated by annealing at 950° C. for 20 min in an $N_2$ ambient. Finally, the contact pads were covered by a 50 nm thick Au film and a 10 nm thick Ni buffer layer. The SiNW-FET thus obtained was soaked in an ethanol bath for 10 min and then washed by a solution containing 25% hydrogen peroxide and 75% sulfuric acid for 10 min to remove organic contaminants.

Figure 3:
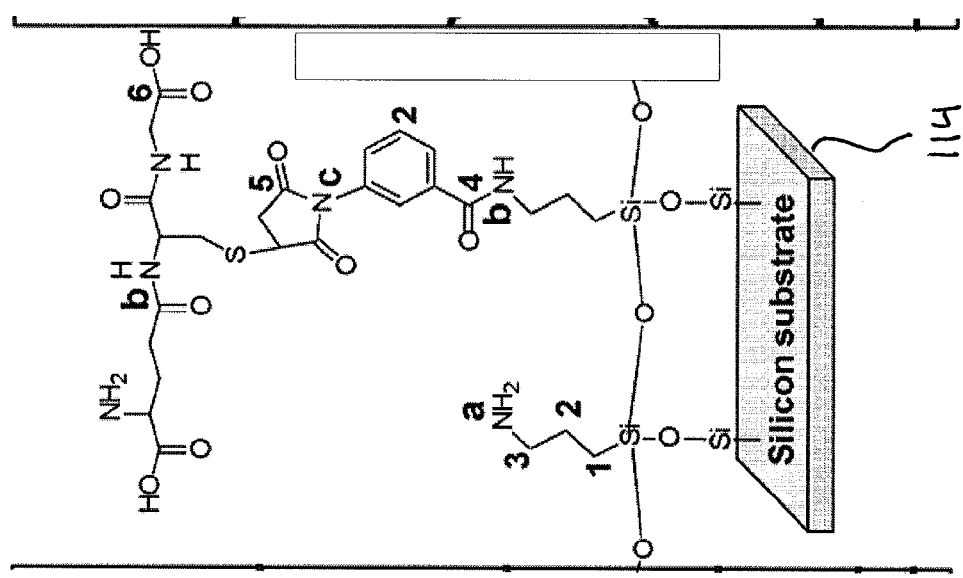
FIG. 3 is a diagram showing a process of attaching GSH to a nanowire covalently.

GSH was then immobilized onto a SiNW-FET prepared by either method described above via a step-wise process as follows to produce GSH/SiNW-FET. See also FIG. 3. First, the SiNW-FETs were immersed in 1 mM ethanolic solution of 3-aminopropyl-trimethoxysilane (APTMS) for 1 h to form a self-assembled monolayer of APTMS. Next, the SiNW-FET covered by the APTMS layer was then soaked in a 1 mM solution of 3-maleimidobenzoic acid N-hydroxysuccinimide ester (MBS) for 2 hours to allow formation of an amide bond between MBS and a free amine of APTMS. Finally, the SiNW-FET coated by APTMS/MBS was placed in a GSH-containing 1×phosphate solution (PS, consisting of 0.76_mM $Na_2HPO_4$ and 0.24_mM $NaH_2PO_4$) at pH 7.0 for 2 hours under conditions allowing formation of a thioether bond between GSH and MBS.

A polydimethylsiloxane (PDMS) microfluidic channel, aligned to couple with the GSH/SiNW-FET, was designed to deliver the GST-containing solution to the location of the GSH/SiNW-FET by a syringe pump. GST association with GSH/SiNW-FET was confirmed by electron spectroscopy for chemical analysis (ESCA).

II. Examining Association/Dissociation of GST/GSH on a GST/GSH-SiNW-FET.

The conventional real-time electrical measurements were performed to examine whether the GSH/GST associate in a reversible manner in the GSH/GST-SiNW-FET described above. See, e.g., Lin et al., *Proc. Natl. Acad. Sci. USA* 107, 1047-1052, 2010. The conductance of the GSH/SiNW-FET, before and after GST association, was measured at a source-drain voltage ($V_{ds}$) of 30 mV, a modulation frequency of 79 Hz, and a time constant of 100 ms using a detection system that combined a current preamplifier and a lock-in amplifier. Furthermore, an Ag/AgCl electrode coupled to the PDMS microchannel was used as a solution gate and was kept at ground potential throughout the real-time electrical measurements in order to minimize noise in the system.

Figure 4:
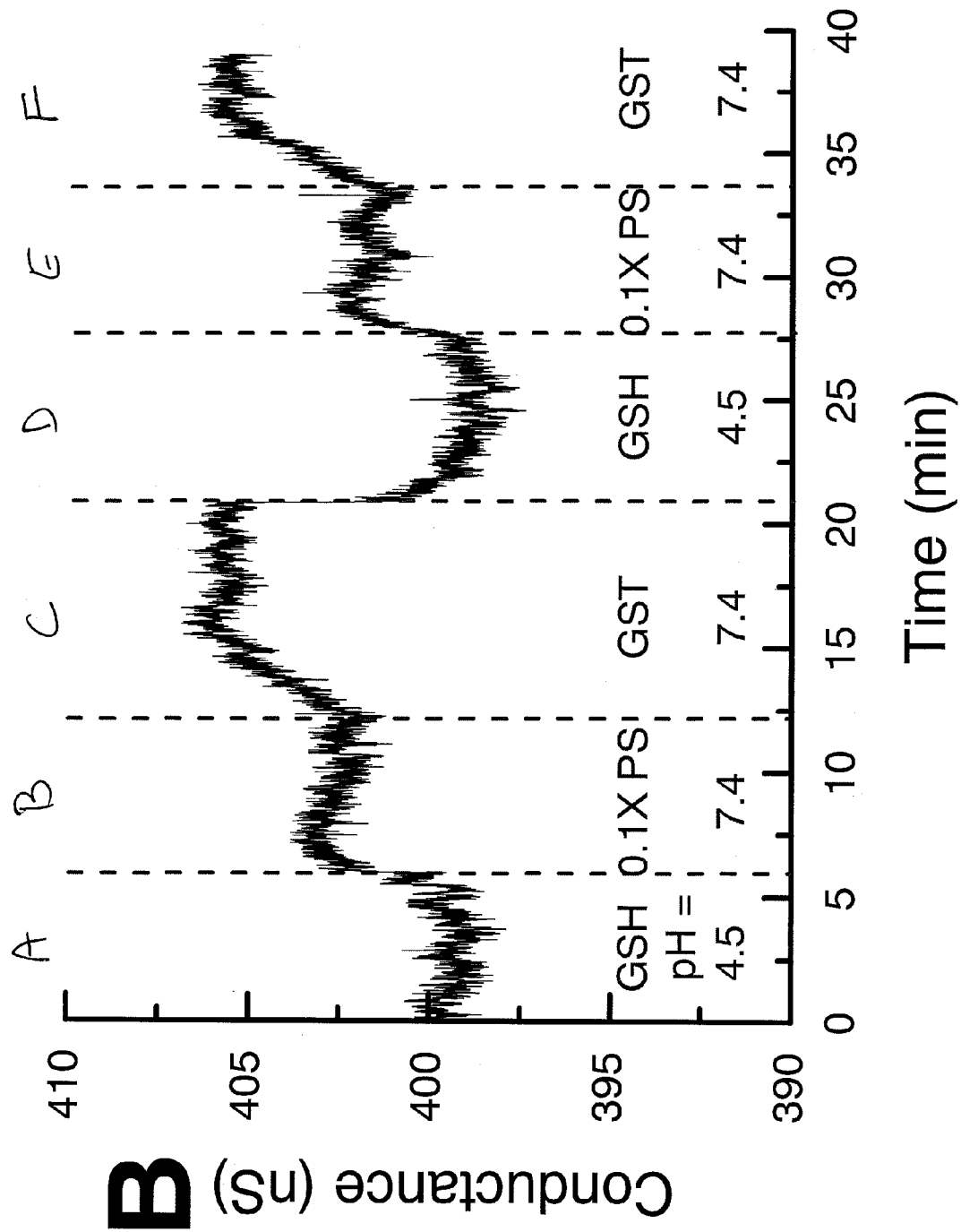
FIG. 4. is a graph showing conductance changes upon association/dissociation of GST with a GSH immobilized NW-FET.

As shown in FIG. 4, panels B and C, the conductance of the GSH/SiNW-FET increased after it was in contact with GST. The GST-associated GSH/SiNW-FET was then washed by a 0.1×PS containing 1 mM GSH (pH 4.5) to dissociate the interaction between GSH and GST on the SiNW-FET. The conductance of the GSH/SiNW-FET returned to the level before its association with GST. See FIG. 4, panels D and E. This indicates that GSH and GST interact with each other in a reversible manner. In other words, the GST molecules bound to the GSH/SiNW-FET were released by a GSH-containing solution. After being re-exposed to a GST-containing solution, the conductance of the GSH/SiNW-FET increased again to a level similar to that observed after its initial contact with GST, indicating that GST was again associated with GSH on the SiNW-FET. See FIG. 4, panel F. Unexpectedly, after 30 cycles of repeated association-dissociation, the GSH/SiNW-FET yielded the same ESCA spectrum pattern as the original GSH/SiNW-FET. This result indicates that the GSH/SiNW-FET described above can be reused for at least 30 times.

EXAMPLE 2

Detecting and Quantifying Troponin I(TnI) with a Calmodulin(CaM)-GST Associated GSH/SiNW-FET The GSH/SiNW-FET was used to detect presence of TnI, using CaM fused with GST as a bait. First, a fusion protein containing CaM and GST was prepared via conventional recombinant technology. The CaM/GST fusion protein was dissolved in a 0.1×PS at a concentration of 200 nM. The CAM-GST solution was then pumped into a PDMS microfluidic channel (6.25×0.5×0.05 $mm^3$), which was designed to couple with the GSH/SiNW-FET, through a syringe pump at a flow rate of 0.3 mL/hr for 30 min to produce a CaM-GST associated GSH/SiNW-FET.

The CaM-GST associated GSH/SiNW-FET was exposed to a 0.1×PS containing TnI (231 nM) and $Ca^{2+}$ ($10^{-4}$ M). Real-time electrical measurements were performed to monitor the conductance levels of the SiNW-FET before and after the exposure. A conductance change was observed, indicating that TnI was bound to the CaM-GST associated GSH/SiNW-FET. The SiNW-FET was then washed first by a 0.1×PS $Ca^{2+}$-free buffer and then a GSH-containing solution to release the CaM-GST from the GSH on the SiNW-FET, thereby reproducing the GSH/SiNW-FET.

Figure 5:
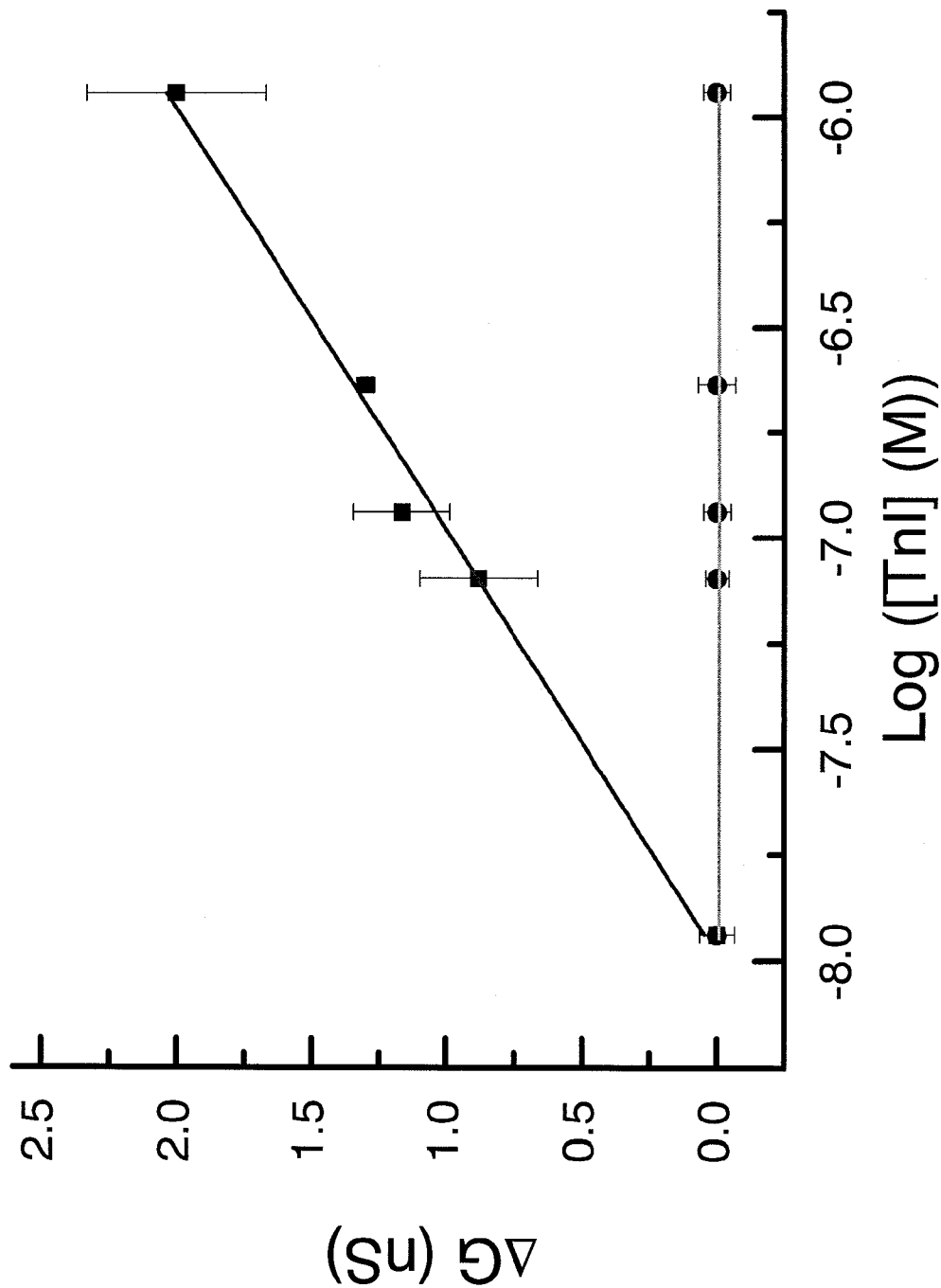
FIG. 5. is a chart showing a linear correlation between the levels of conductance changes of a GSH immobilized NW-FET and the concentrations of TnI protein, which binds to the GSH immobilized NW-FET via TnI/CaM-GST/GSH interaction.

The correlation between TnI concentrations and levels of conductance changes of the CaM-GST-associated GSH/SiNW-FET was examined as follows. The SiNW-FET was in contact with a 0.1×PS solution containing TnI at various concentrations and $10^{-4}$ M $Ca^{2+}$. The conductance change of the GSH/SiNW-FET at each TnI concentration was determined by real-time electrical measurements described above. The results thus obtained show that, with certain range, the log values of TnI concentrations and GSH/SiNW-FET conductance changes are in linear correlation. See FIG. 5. This indicates that the CaM-GST-associated GSH/SiNW-FET can be used to quantify TnI in a sample.

EXAMPLE 3

Figure 6:
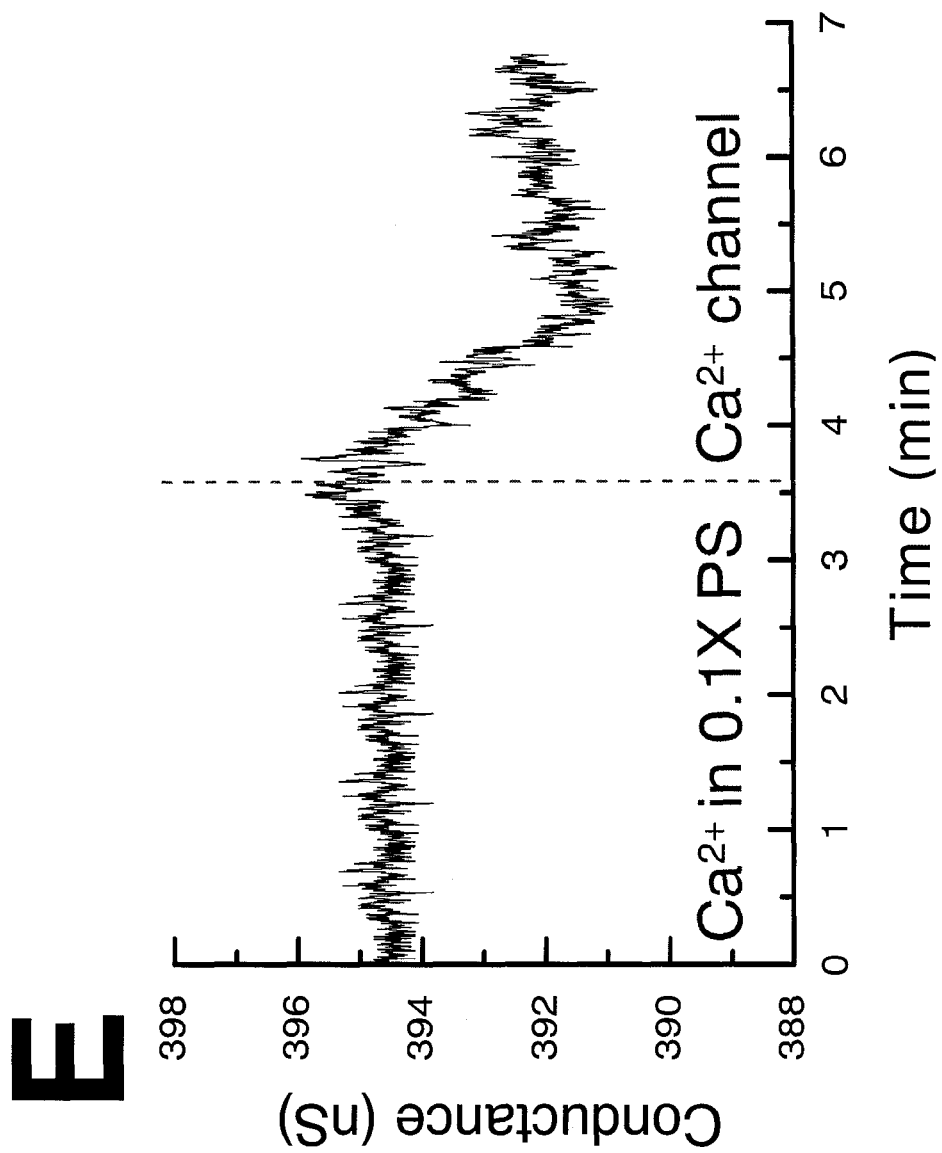
FIG. 6. is a graph showing a conductance change of a GSH immobilized NW-FET upon binding to membrane-bound N-type voltage-gated $Ca^{2+}$ channel (VGCC) protein via VGCC/CaM-GST/GSH interaction.

Using a CaM-GST-Associated GSH/SiNW-FET for Probing N-Type Voltage-Gated $Ca^{2+}$ Channels (VGCC) Present in a Biosample 293T cells transfected with VGCC, a membrane protein, were suspended in phosphate buffered saline (1×PBS, consisting of 137 mM NaCl, 2.7_mM KCl, 10_mM $Na_2HPO_4$, and 2 mM $KH_2PO_4$ at pH 7.4). The cells were sonicated and centrifuged, the membrane fraction collected. After being resuspended and diluted in 0.1×PS containing $Ca^{2+}$, the membrane fraction (1.7 µg/µL) was delivered through a PDMS microfluidic channel onto the surface of a CaM-GST associated GSH/SiNW-FET. The conductance of the SiNW-FET decreased after its contacting with the membrane fraction, indicating that N-type VGCCs on the membranes bound to the CaM of the CaM-GST associated GSH/SiNW-FET. See FIG. 6. This result demonstrates that the GSH/SiNW-FET can be used to detect presence of a target molecule (e.g., VGCC) via association with a conjugate containing GST and a bait molecule (e.g., CaM) that binds to the target molecule.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A reusable field effect transistor system for detecting a biomolecular interaction, the system comprising:
    a field effect transistor containing a nanowire,
    a docking molecule covalently linked to the nanowire, and
    a conjugate containing an anchor molecule and a bait molecule, wherein the docking molecule binds to the anchor molecule at an association constant of $10^5$ to $10^9$ $M^{-1}$.

2. The system of claim 1, wherein the docking molecule is a member of a molecule pair selected from the group consisting of glutathione/glutathione S-transferase, maltose/maltose binding protein, imidazole/polyhistidine, chitin/chitin binding protein, calcium/calmodulin, and covalent yet dissociable peptide/InaD protein.

3. The system of claim 2, wherein the docking molecule is glutathione.

4. The system of claim 1, wherein the bait molecule is selected from the group consisting of protein, nucleic acid, and polysaccharide.

5. The system of claim 1, wherein the anchor molecule and the bait molecule are proteins and the conjugate is a fusion protein containing both.

6. The system of claim 5, wherein the docking molecule is glutathione and the anchor molecule is glutathione S-transferase.

7. The system of claim 1, wherein the nanowire is made of silicon, carbon, tin dioxide, or indium oxide.

8. A method for detecting the presence of a target molecule in a sample, the method comprising:
    providing the system of claim 1, in which the docking molecule is bound to the conjugate containing the anchor molecule and a bait molecule capable of binding to the target molecule,
    contacting the system with a sample suspected of containing the target molecule, and
    detecting a conductivity change of the field effect transistor in the system after the contacting step; wherein observation of a conductivity change indicates presence of the target molecule in the sample.

9. The method of claim 8, wherein the target molecule is a protein molecule, a nucleic acid molecule, a polysaccharide molecule, or a lipid molecule.

10. The method of claim 8, wherein the bait molecule is selected from the group consisting of protein, nucleic acid, and polysaccharide.

11. The method of claim 8, wherein the anchor molecule and the bait molecule are proteins and the conjugate is a fusion protein containing both.

12. The method of claim 8, wherein the docking molecule is a member of a molecule pair selected from the group consisting of glutathione/glutathione S-transferase, maltose/maltose binding protein, imidazole/polyhistidine, chitin/chitin binding protein, calcium/calmodulin, and covalent yet dissociable peptide/InaD protein, and the anchor molecule is the other member of the molecule pair.

13. The method of claim 12, wherein the docking molecule is glutathione and the anchor molecule is glutathione S-transferase.

14. The method of claim 13, wherein the bait molecule is a protein fused with the glutathione S-transferase.

15. The method of claim 8, further comprising correlating a level of the conductivity change with a concentration of the target molecule in the sample.

16. The method of claim 15, wherein the docking molecule is glutathione, the anchor molecule is glutathione S-transferase, and the bait molecule is a protein fused with the glutathione S-transferase.

17. The method of claim 8, further comprising, after the detecting step, washing the field effect transistor with a solution containing the docking molecule to release the conjugate bound to the field effect transistor.

18. The method of claim 17, wherein the docking molecule is glutathione, the anchor molecule is glutathione S-transferase, and the bait molecule is a protein fused with the glutathione S-transferase.

19. The system of claim 1, wherein the docking molecule is in a solution and, as such, is dissociable from the anchor molecule.

20. The system of claim 19, wherein the system is reusable for at least 30 times.

* * * * *